United States Patent
Graehlert et al.

(10) Patent No.: US 10,228,329 B2
(45) Date of Patent: Mar. 12, 2019

(54) ARRANGEMENT FOR DETERMINING PROPERTIES AND/OR PARAMETERS OF A SAMPLE AND/OR OF AT LEAST ONE FILM FORMED ON THE SURFACE OF A SAMPLE

(71) Applicant: FRAUNHOFER-GESELLSCHAFT ZUR FOERDERUNG ANGEWANDTEN FORSCHUNG E.V., Munich (DE)

(72) Inventors: Wulf Graehlert, Dresden (DE); Philipp Wollmann, Dresden (DE); Florian Gruber, Dresden (DE)

(73) Assignee: FRAUNHOFER-GESELLSCHAFT ZUR FOERDERUNG ANGEWANDETEN FORSCHUNG B.V., Munich (DE)

( * ) Notice: Subject to any disclaimer, the term of this patent is extended or adjusted under 35 U.S.C. 154(b) by 0 days.

(21) Appl. No.: 15/321,465

(22) PCT Filed: Jun. 22, 2015

(86) PCT No.: PCT/EP2015/063984
§ 371 (c)(1),
(2) Date: Dec. 22, 2016

(87) PCT Pub. No.: WO2015/197555
PCT Pub. Date: Dec. 30, 2015

(65) Prior Publication Data
US 2017/0212056 A1    Jul. 27, 2017

(30) Foreign Application Priority Data
Jun. 23, 2014  (DE) .......................... 10 2014 009 372

(51) Int. Cl.
*G01N 21/84*    (2006.01)
*G01N 21/31*    (2006.01)
(Continued)

(52) U.S. Cl.
CPC ..... *G01N 21/8422* (2013.01); *G01B 11/0625* (2013.01); *G01N 21/21* (2013.01); *G01N 21/31* (2013.01); *G01N 2021/8438* (2013.01)

(58) Field of Classification Search
CPC .... G01N 21/8422; G01N 21/21; G01N 21/31; G01N 2021/8438; G01B 11/0625
See application file for complete search history.

(56) References Cited

U.S. PATENT DOCUMENTS

| 7,301,649 | B2* | 11/2007 | Fabrikant | G01N 21/21 250/225 |
| 2001/0052979 | A1* | 12/2001 | Treado | G01B 11/2545 356/326 |

(Continued)

FOREIGN PATENT DOCUMENTS

| DE | 102006034776 B3 | 6/2008 |
| EP | 2840368 A1 | 2/2015 |

(Continued)

OTHER PUBLICATIONS

Fraunhofer-Institut fur Werstoff- und Strahitechnik IWS [Fraunhofer Institute for Material and Beam Technology]: annual report 2013. Dresden, 2014. 1, 21, 30, 31.

*Primary Examiner* — Dominic J Bologna
(74) *Attorney, Agent, or Firm* — Jacobson Holman, PLLC.

(57) ABSTRACT

An arrangement for determining characteristics or parameters of a sample, or a layer formed on or in the sample, has detectors, spatially resolving spectral analysis of electromagnetic radiation within a wavelength interval, provided in rows or in a row and column arrangement, whereby electromagnetic radiation emitted from a broadband radiation source is incident on the detectors after reflecting off, and/or passing through, the sample, or layer formed on or in the sample, upon which is observed a homogeneous intensity of the electromagnetic radiation, and an electronic evaluation (Continued)

unit connected to the detectors compares the spatially-resolved and wavelength-resolved signals detected by the detectors with a theoretical wavelength dependent progression of the respective radiation intensities obtained through simulation or with a progression obtained by calibration on a known sample, in order to obtain information for the measurement position detected, and determine the spatially-resolved distribution of the characteristics or parameters.

12 Claims, 1 Drawing Sheet

(51) Int. Cl.
*G01B 11/06* (2006.01)
*G01N 21/21* (2006.01)

(56) References Cited

U.S. PATENT DOCUMENTS

| | | | | |
|---|---|---|---|---|
| 2007/0019194 | A1* | 1/2007 | Chen | G01J 3/02 356/328 |
| 2008/0245979 | A1* | 10/2008 | Banton | G01N 21/57 250/559.4 |
| 2010/0108873 | A1* | 5/2010 | Schwertner | G01B 11/2504 250/252.1 |
| 2015/0131090 | A1* | 5/2015 | Osumi | G01J 3/504 356/300 |

FOREIGN PATENT DOCUMENTS

| | | | |
|---|---|---|---|
| WO | WO 2013/157641 A1 | 10/2013 | |
| WO | WO 2013157641 A1 * | 10/2013 | G01J 3/504 |

* cited by examiner

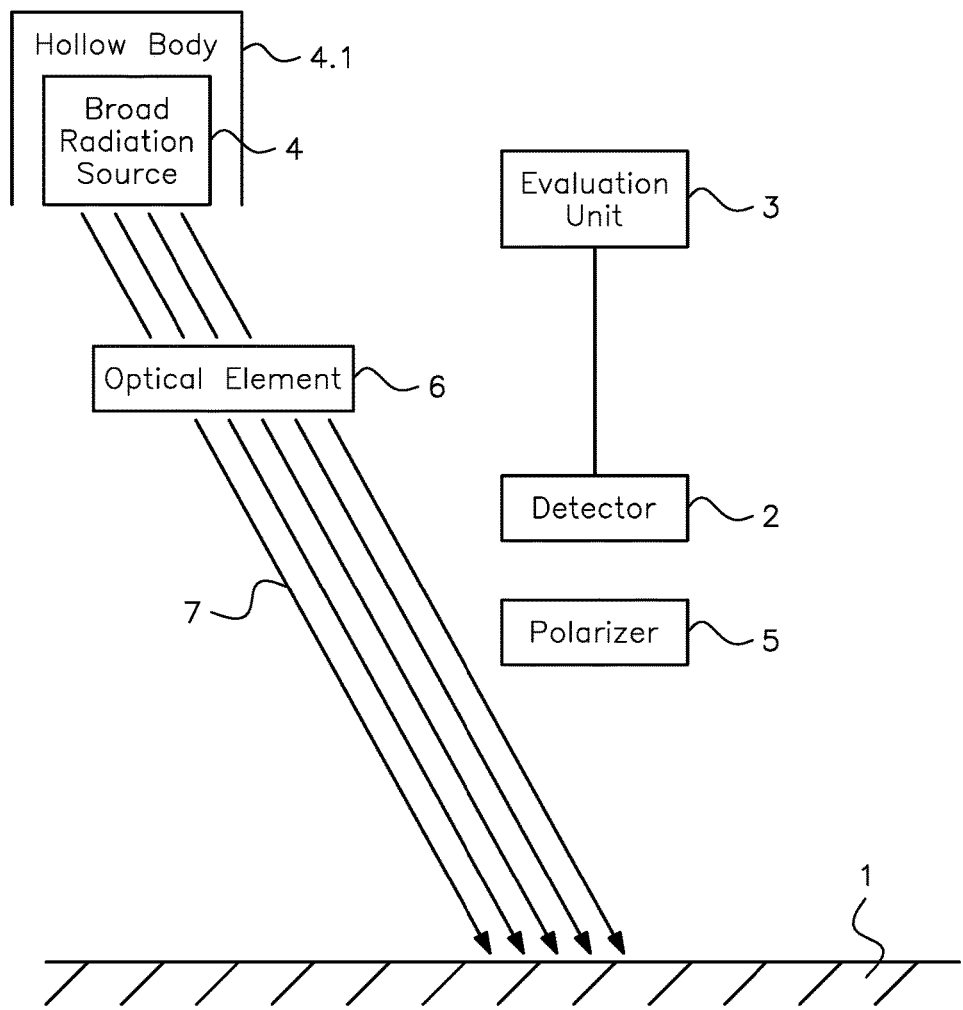

ARRANGEMENT FOR DETERMINING PROPERTIES AND/OR PARAMETERS OF A SAMPLE AND/OR OF AT LEAST ONE FILM FORMED ON THE SURFACE OF A SAMPLE

The invention relates to an arrangement for determining properties and/or parameters of a sample and/or of at least one film formed on or at a surface of a sample. In this respect, a sample should be understood as solid bodies, solid bodies coated with at least one film or as elements formed from a plurality of layers arranged over one another.

Thin films (single- or multi systems on defined substrates) are essentially known per se in a plurality of applications, e.g. semiconductor films, wear-protection films, optical films, etc. The observation of predefined film parameters/properties in predefined tolerance ranges is required for their function. In this respect, the important parameters are the film thickness(es), the optical refractive index/indices, the absorption constant(s) at specific wavelengths, or the parameters for describing their curves over a specific wavelength range. Further properties of layers, but also of homogeneous samples, can be the number of charge carriers contained per surface or volume (charge carrier concentration) that are present or the number of inhomogeneities or defects contained (particulates, inclusions, etc.).

It is very frequently necessary to determine these parameters reliably and in a short time over the total surface of a sample. In this respect, the distribution of the above parameters should be able to be determined with spatial resolution over the total sample surface. In this respect, a statistically secured statement on the total sample should be possible.

Different dedicated measurement processes are typically used for the above-named properties and parameters; however, they are mostly single-point measurements in which a spatial resolution (x or x-y) of the respective measurement parameter can be achieved by a sample movement or sensor movement (mapping). A visual representation of the detected measured values has to be prepared separately in a complex and/or expensive manner.

The film thickness distribution can thus typically e.g. be determined in an interferometric manner. Ellipsometry can be used for other ones of the above-named parameters or properties. However, this is only possible simultaneously for one wavelength, whereby the accuracy and/or the required time effort is/are disadvantageous.

It is therefore the object of the invention to provide possibilities for a determination of the lateral distribution of properties and/or parameters of samples or of layers formed on samples or present in samples in a short time and with very high accuracy, with a visual representation of the results preferably being possible with a small additional effort.

This object is achieved in accordance with the invention by an arrangement having the features described below. Advantageous embodiments and further developments of the invention can be realized using features designated below.

Thus, in accordance with the invention, an arrangement determines properties and/or parameters of a sample and/or of at least one film formed on a surface of a sample, in which a plurality of detectors that are configured for a spatially resolved spectral analysis of electromagnetic radiation within a wavelength interval are arranged in a row arrangement or in a row and column arrangement; and the detectors are connected to an electronic evaluation unit and are arranged such that electromagnetic radiation emitted by a broadband radiation source is incident onto the detectors either after a reflection at the surface of the sample, at a film formed on the sample or at the surface of a film within the sample and/or after passing through a sample transparent to the electromagnetic radiation, wherein the irradiation takes place such that a homogenous intensity of the electromagnetic radiation is observed on a surface from which the electromagnetic radiation is reflected or is transmitted by the surface; and the electronic evaluation unit is configured such that the measured signals of the detectors detected with spatial and wavelength resolution within a wavelength interval are compared with a theoretical wavelength-dependent curve of the respective radiation intensities obtained by simulation or with as curve obtained by a calibration at least one known sample to obtain a statement for determining at least one property or at least one parameter of the sample or of at least one film formed on or at the sample for the detected measurement positions and thus to obtain the spatially resolved distribution of at least one property or of at least one parameter of the sample or of at least one film formed on or at the sample.

BRIEF DESCRIPTION OF THE DRAWING

FIG. 1 schematically illustrates the invention

The arrangement in accordance with the invention, as shown in FIG. 1, for determining properties and/or parameters of a sample (1) and/or of at least one film formed on a surface of a sample or present at the sample has a plurality of detectors (2) that are configured for a spatially resolved spectral analysis of electromagnetic radiation(7) within a wavelength interval. These detectors are arranged in a row arrangement or in a row and column arrangement. The detectors are connected to an electronic evaluation unit (3) and are arranged such that electromagnetic radiation emitted by a broadband radiation source (4) is incident on the detectors either after a reflection at the surface of the sample, at a film formed on the sample or at the surface of a film within the sample and/or after passing through a sample transparent to the electromagnetic radiation. The irradiation takes place in this respect such that a homogenous intensity of the electromagnetic radiation is observed on a surface from which the electromagnetic radiation is reflected or is transmitted by the surface. The respective surface to be detected simultaneously should therefore be irradiated with a homogenous intensity.

The electronic evaluation unit is configured such that the measured signals of the detectors detected with spatial and wavelength resolution within a wavelength interval are compared with a theoretical, wavelength-dependent curve of the respective radiation intensities obtained by simulation or with a curve obtained by a calibration at least one known sample to obtain a statement for determining at least one property or at least one parameter of the sample or at least one film formed on the sample or present at the sample. The wavelength interval in which the evaluation takes place should be at least a subset of the wavelength interval of the electromagnetic radiation used for the irradiation.

At least 30 detectors, preferably at least 100 detectors, should be arranged in one row in this respect.

The irradiation of the surface should take place at least one angle in the range of 0° to <90° with respect to the normal of the surface of the sample. When irradiating through a sample transparent to the electromagnetic radiation, the angle of at least approximately 0° to the sample normal should be observed; that is, the radiation should be directed as perpendicular as possible onto the surface of the sample to keep the reflected portion as small as possible. The irradiation and the detection can also be carried out at a varying angle of incidence of the electromagnetic radiation. As already expressed, angles of incidence can be selected in this respect in the range from 45° to a maximum of 89°. Angles of incidence of 60° to 80° are preferred when reflected radiation is to be detected, independently of whether a constant angle of incidence or different angles of incidence is/are to be used.

The irradiation or the detection can also take place using polarized electromagnetic radiation. In this case, the alignment of the polarization plane can be changed and the electromagnetic radiation can be emitted at differing polarization and/or can be correspondingly detected.

The film thickness(es), the optical refractive index/indices, their wavelength-dependent curves, the absorption constant(s), their wavelength-dependent curves, the surface quality of the sample or of at least one film formed on the sample, the charge carrier concentration and/or the number and/or size of defects/particulates or inhomogeneities in the sample or in at least one film can be detected with the invention. A thickness determination and a surface quality determination can thus be carried out simultaneously, for example. The surface roughness can be determined in this process. The size of individual defects or inhomogeneities (differences in the material composition) and/or their number per surface can also be determined.

The detectors and the sample can in particular be moved along at least one axis relative to one another, and in this process preferably at a constant spacing from one another, with large-surface samples. A sample can thus be moved in one axis with statically fixed detectors and a statically fixed radiation source. It can be moved in an x direction and optionally also in a y direction using a correspondingly movable table on which a sample is arranged. However, an unwinding from roll to roll is also possible when the sample is present as a flexibly deformable material, for example in the form of a film.

Elements shaping the electromagnetic radiation can be present at the radiation source. The radiation source can be a microscope in a simple embodiment. A radiation source (4) shown in FIG. 1 can, however, also be arranged in a hollow body (4.1) from which the electromagnetic radiation can exit diffusely and can be directed onto the surface to be irradiated. The hollow body can be a sphere or a cylinder. A surface to be detected simultaneously should be able to be irradiated homogenously. The wavelength range used should be considered with a radiation source having beam-shaping optical elements (6) when selecting the respectively used optical elements that serve the beam shaping.

A diaphragm avoiding the incidence of scattered electromagnetic radiation can preferably be arranged in front of the detectors in the optical path of the electromagnetic radiation.

Electromagnetic radiation can be emitted by the radiation source whose wavelengths start at UV radiation and end at IR radiation. Radiation from the NIR and IR ranges, that is, from 700 nm to 10,000 nm, is particularly preferred. Where possible, all the wavelengths within the respective interval should be able to be used in a utilized wavelength range for the irradiation. The limits should be predefined solely by the sensitivity range of the detectors used and by the optical properties of the beam-conducting components. With very thin layers, work can preferably be carried out with wavelengths in the UV/VIS range (from 250 nm).

At least one polarizer (5) element, as shown in FIG. 1, with which a direct choice of the polarization of the electromagnetic radiation can be achieved can also be present there or integrated therein.

A sample can also be a multi structure of a plurality of layers formed from different materials. This can, for example, be a substrate on which layers are formed that are at least partly transparent to the used electromagnetic radiation. The substrate can also be correspondingly transparent in this respect. The transparency can relate to a part of the wavelength spectrum of the emitted electromagnetic radiation and/or to a non-absorbed part of the total wavelength spectrum of the radiation.

The detectors used and the electronic evaluation unit as well as optionally the radiation source can also represent a so-called hyper-spectral image system that can be used in the arrangement in accordance with the invention.

The spectra detected simultaneously with spatial resolution (at every detected position) can be evaluated as follows with respect to the material parameters of interest or with respect to its property.

In a first variant A, the total structure can be physically described by means of a parameterized optical model. In this respect, the sample parameters to be determined can be determined by regression (fit) of a spectrum simulated on the basis of the optical model with respect to the measured spectrum, which can e.g. be achieved by linear or non-linear curve fitting or by least squares fitting. If a sufficient fit is not possible, the measured results should be discarded or they can be considered as interference in the film or in the sample surface.

In a variant B, the relationship "spectrum—target parameter(s)"—can be calibrated using samples with known target parameter value(s). The target parameter(s) from every measured spectrum can be determined (at every location) with the aid of this calibration model. Methods of multi-variant, mathematically statistical data evaluation can be used for the calibration such as principle component analysis (PCA) or partial least square analysis (PLS).

In this respect, illumination should be homogenous over the total sample zone to be examined. The intensity fluctuations caused by the sample (and to be evaluated) are otherwise superposed by the lateral intensity fluctuations caused by the irradiation, which produces errors. Microscope optics having homogenous microscope illumination can be used to implement a laterally homogenous light field for the irradiation of a small surface on samples. A "diffuser setup", in particular at least one radiation source that is arranged within a hollow body (e.g. an Ulbricht sphere or a hollow cylinder) can be used for the irradiation for samples of larger surfaces.

When recording spectra at a defined angle of incidence of the electromagnetic radiation, one or more angles of incidence in the range 0°-85° can be used for a reflection setup.

A combination of different measurement conditions can take place. In this respect, transmission/reflection measurement, a combination of different angles of incidence, the use and combination of different polarization levels of the electromagnetic radiation can be combined with one another in the most varied forms.

There is also the possibility of using a plurality of row arrangements or row and column arrangements of detectors that can then be arranged after one another in the direction of movement, for example. These arrangements of detectors can each detect under different measurement conditions.

Detection can take place under different measurement conditions using arrangements of detectors whose line/row is configured by using different optical arrangements (different optical elements) or that can be modified.

A fast characterization of an entire sample can be achieved with respect to a target parameter in a short time using the invention.

The user can, for example, immediately e.g. obtain a "film thickness image" of the sample. A visual representation of defects or of the local charge carrier concentration or of the chemical composition is also possible.

The acquired information can be used for the monitoring of coating processes (inline control), the development of systems and also for quality control (lateral distribution of relevant film parameters).

The invention claimed is:

1. An arrangement, for determining at least one property or parameter of a sample or at least one film formed on a surface of a sample, comprising
   a) a plurality of detectors configured for a spatially resolved spectral analysis of electromagnetic radiation within a wavelength interval and arranged in a row arrangement or in a row and column arrangement, such that electromagnetic radiation emitted by a broadband radiation source, such that a homogenous intensity of the electromagnetic radiation is observed on a surface from which the electromagnetic radiation is reflected or is transmitted by the surface, is incident onto the detectors either after a reflection at the surface of the sample, at a film formed on the sample, or at the surface of a film within the sample after passing through a sample transparent to the electromagnetic radiation, the detectors connected to
   b) an electronic evaluation unit configured such that the measured signals of the detectors detected with spatial and wavelength resolution within a wavelength interval are compared with a theoretical wavelength-dependent curve of the respective radiation intensities obtained by simulation or with as curve obtained by a calibration at least one known sample to obtain a statement for determining the at least one property or parameter for the detected measurement positions and thus to obtain the spatially resolved lateral distribution of the at least one property or parameter.

2. The arrangement in accordance with claim 1, characterized in that irradiation of the surface takes place at least one angle in the range from 0° to <90° with respect to the normal of the surface of the sample.

3. The arrangement in accordance with claim 1, characterized in that the angle of incidence of the electromagnetic radiation is variable in the range from 60° to 80°, with the detection and evaluation able to be carried out at different angles of incidence.

4. The arrangement in accordance with claim 1 further comprising a polarizer configured for carrying out the detection and evaluation and having a defined known polarization plane with respect to the place of incidence.

5. The arrangement in accordance with claim 1, characterized in that the lateral distribution is determinable for
   film thickness,
   film optical refraction constant or optical refraction constant wavelength-dependent curve,
   film absorption constant or absorption constant wavelength-dependent curve,
   surface quality of the sample and the at least film,
   sample charge carrier concentration,
   number or size of inhomogeneities in the sample, or
   number or size of inhomogeneities in the at least one film.

6. The arrangement in accordance with claim 1, characterized in that the detectors and the samples are movable along at least one axis relative to one another.

7. The arrangement in accordance with claim 1, characterized in that the detectors and the samples are movable along at least one axis relative to one another at a constant spacing from one another.

8. The arrangement in accordance with claim 1, characterized in that the radiation source has optical elements shaping the electromagnetic radiation.

9. The arrangement in accordance with claim 1, characterized in that the radiation source diffusely emits electromagnetic radiation over the sample surface of the at least one film surface.

10. The arrangement in accordance with claim 1, characterized in that the radiation source is arranged within a hollow body.

11. The arrangement in accordance with claim 1 further comprising a diaphragm avoiding the incidence of scattered electromagnetic radiation arranged in front of the detectors in the optical path of the electromagnetic radiation.

12. The arrangement in accordance with claim 1, characterized in that the sample is a multilayer structure of a plurality of films formed from different materials.

* * * * *